United States Patent [19]

Mikayama et al.

[11] Patent Number: 5,264,209
[45] Date of Patent: Nov. 23, 1993

[54] MODIFIED HIL-6

[75] Inventors: Toshihumi Mikayama, Gunma; Toshihiko Kadoya, Takasaki; Makoto Kakitani, Maebashi; Hideo Inoue, Takasaki, all of Japan

[73] Assignee: Kirin-Amgen, Inc., Thousand Oaks, Calif.

[21] Appl. No.: 632,070

[22] Filed: Dec. 21, 1990

[30] Foreign Application Priority Data

Feb. 13, 1990 [JP] Japan .................. 2-32273
Aug. 22, 1990 [JP] Japan .................. 2-222353
Sep. 21, 1990 [JP] Japan .................. 2-250460

[51] Int. Cl.$^5$ ............ C07K 15/06; A61K 37/02
[52] U.S. Cl. ................ 424/85.2; 530/351; 530/406; 530/410
[58] Field of Search ........ 424/85.2; 530/351, 406, 530/410

[56] References Cited

U.S. PATENT DOCUMENTS 4,179,337 12/1979 Davis et al. .
4,766,106 8/1988 Katre et al. .
4,791,192 12/1988 Nakagawa et al. .
4,810,643 3/1989 Souza .
4,847,325 7/1989 Shadle et al. .
4,904,584 2/1990 Shaw .

FOREIGN PATENT DOCUMENTS 210761 2/1987 European Pat. Off. .
236987 9/1987 European Pat. Off. .
247860 12/1987 European Pat. Off. .
0257406 3/1988 European Pat. Off. .
335423 10/1989 European Pat. Off. .
0363083 4/1990 European Pat. Off. .
60938 3/1988 Japan .
88/00206 1/1988 PCT Int'l Appl. .
00056 1/1987 World Int. Prop. O. .

OTHER PUBLICATIONS

Katre et al., Proc. Natl. Acad. Sci. U.S.A., 84, pp. 1487–1491 (1987).
Koerholz et al., Eur. J. Haematol., 42(5), pp. 417–424 (1982).
Brakenhoff, et al., The Journal of Immunology, 143:1175–1182 (1989).
Castell, et al., Eur. J. Biochem., 177:357–361 (1988).
Goodson, et al., Bio/Technology, 8:343–346 (1990).
Haegeman, et al., Eur. J. Biochem., 159:625–632 (1986).
Hirano, et al., Proc. Nat'l. Acad. Sci. U.S.A., 82:5490–5494 (1985).
Ishibashi, et al., Blood, 74:1241–1244 (1989).
Kishimoti, et al., Ann. Rev. Immunol., 6:485–512 (1988).
Okada, et al., J. Exp. Med., 157:583–590 (1983).
Stocks, et al., Analytical Biochemistry, 154:232–234 (1986).
Inada et al. (1986) Trends in Biotech., Mar., pp. 68–73.

*Primary Examiner*—Robert A. Wax
*Assistant Examiner*—Keith C. Furman
*Attorney, Agent, or Firm*—Marshall, O'Toole, Gerstein, Murray & Borun

[57] ABSTRACT

Provided are PEGylated "interleukin-6" derivatives (PEG IL-6) having an extended plasma half-life, as well as enhanced in-vivo IL-6 biological activities.

Methods for producing the modified glycosylated and unglycosylated IL-6 proteins or polypeptides, as well as, for their use in treating hematopoietic disorders and difficiencies, particularly acute thrombocytopenia, are also provided.

20 Claims, 4 Drawing Sheets

MODIFIED HIL-6

FIELD OF THE INVENTION

The present invention relates to modified glycosylated and unglycosylated proteins and polypeptides possessing interleukin-6 (hereafter referred to as IL-6) activities where the modification comprises chemical modification of at least one amino group or carboxyl group on the proteins and polypeptides. The invention also relates to a process for producing the modified proteins or polypeptides, and to their use in treating haematopoietic disorders and deficiencies, particularly acute thrombocytopenia.

BACKGROUND OF THE INVENTION

Interleukin-6 is a multi-functional cytokine (Kishimoto, T. and T. Hirano, *Ann. Rev. Immunol.*, 6:485 (1988)). Included among its diverse biological activities is the induction of the terminal differentiation of B cells to plasma cells, the differentiation of killer T cells and nerve cells, as well as the acute phase protein synthesis of hepatocytes. It also stimulates the growth of hybridoma/plasmacytoma/myeloma cells, T cells, and hematopoietic stem cells. Differentiation inducing activity on megakaryocytes, leading to the production of platelets, has also been reported recently (Ishibashi, T., et al., *Blood* 74:1241, (1989)).

One example of glycosylated proteins or polypeptides possessing interleukin-6 activities is human interleukin-6 (hereafter referred to as hIL-6). There are a number of reports on processes for producing hIL-6; for example, production by human T cell hybridoma cells (Okada, M., et al., *J. Exp. Med.*, 157:583 (1983)) or by human T cells transformed with human T cell leukemia virus (Japanese patent application, KOKAI NO. 61-115024). Human IL-6 may also be produced by recombinant DNA technologies which comprise transforming mammalian or bacterial cells with a vector carrying a DNA sequence encoding hIL-6 and then culturing these cells to obtain recombinant hIL-6. The resultant hIL-6 is a glycosylated protein if produced by mammalian cells, and an unglycosylated polypeptide if produced by bacterial cells. Both forms have been demonstrated to have interleukin-6 activities (EP 257406; WO 88/00206).

The mature fully functional hIL-6 polypeptide has 184 amino acid residues as predicted from the nucleotide sequence of its cDNA. However, polypeptides with one or more additional amino acid residues or (at most) 27 amino acid deletions at their N-terminus, as well as polypeptides with at most 50 amino acid deletions (or substitutions) at their C-terminus, are known to retain IL-6 activity (EP 257406; WO 88/00206; EP 363083; Brakenhoff, J. P. J., *J. Immunol.*, 143:1175 (1989)).

Several methods have been used to try to prolong the plasma half-life of certain intravenously administered high molecular weight polypeptides. These include modification of the polypeptide with polyethylene glycol (PEG), dextran, poly[Glu-Lys], pullulan, modified polyaspartate or fatty acids, as well as coupling with gamma-globulin. The chemical modification with PEG of a few non-human derived enzymes, such as asparaginase, superoxide dismutase, or uricase, resulted in increased plasma half-life. However, a number of problems have been observed with PEGylation. Acylation of tyrosine residues on the protein can result in a lowering of the biological activity of the protein; certain PEG-protein conjugates are insufficiently stable and therefore find no pharmacological use; certain reagents used for PEGylation are insufficiently reactive and therefore require long reaction times during which protein denaturation and/or inactivation can occur. Also, the PEGylating agent may be insufficiently selective. Difficulties can also arise as a result of the hydrophobicity of the protein to be PEGylated; in an aqueous medium hydrophobic proteins resist PEGylation at physiological pH. The criteria for effective PEGylation include not only whether the conjugated molecule has a combination of increased serum half-life and decreased immunogenicity, but also whether it is in fact a more potent pharmacological agent than its unmodified parent molecule. Given the broad range of differences in the physical characteristics and pharmacokinetics among proteins, it is impossible to predict in advance whether a protein can be successfully PEGylated and/or whether the PEGylated protein will still retain its biological activity without inducing untoward immunological responses.

For example, in WO87/00056, relating to the solubilization of proteins for pharmaceutical compositions using polymer conjugation, the adverse effect of PEGylation on the in vitro activity of IL-2 is described in Example IIB (Table I, page 20). Example IC (page 19) references the IL-2 cell proliferation bioassay used. The results demonstrate that as more amino groups of the IL-2 are substituted with PEG, the PEGylated IL-2 undergoes a nearly 10-fold decrease in activity as compared to the activity of unmodified IL-2.

The covalent modification of lysine residues causes a reduction in bioactivity of certain proteins. Lysine modification with activated PEG-esters is random, difficult to control, and often results in reduced bioactivity of the modified protein. Goodson, R., et al., *Bio/Technology*, 8:343 (April 1990).

U.S. Pat. No. 4,904,584 (Feb. 27, 1990) describes a process for preparing PEGylated polypeptides. However, the process requires a premodification of the polypeptides by first preparing LDVs (lysine depleted variants) to obtain a polypeptide having a "suitable" number of reactive lysine residues. No evidence is presented that PEGylated derivatives were actually obtained; nor is their any evidence that these proposed modified polypeptides retained any biological activity. Further, there is no exemplification of the production of PEG-IL-6 nor any exemplification of retained activity.

As the in vivo half-life of IL-6 in blood is very short (Castell, J. V. et al., *Eur. J. Biochem.*, 177:357 (1988)), it is desirable to increase hIL-6 plasma half-life and to thereby improve the pharmacokinetics and therapeutic efficacy of IL-6. To date, however, no one has been successful in so doing.

SUMMARY OF THE INVENTION

The present invention provides chemically modified glycosylated and unglycosylated proteins or polypeptides possessing a prolonged plasma half-life and improved in vivo IL-6 activities, particularly platelet producing activity, in primates, and especially in humans.

According to the invention, IL-6 is derivatized with polyethylene glycol (PEG) to produce PEG-IL-6 having prolonged plasma half-life and enhanced in vivo IL-6 biological activity. The IL-6 may be either glycosylated IL-6, unglycosylated IL-6, or biologically active fragments of either glycosylated or unglycosylated IL-6. Preferred amino acid sequences for IL-6 are set forth in the Sequence Listing and identified as Sequence Id Nos. 1, 2, and 3. The IL-6 can be either naturally or synthetically produced, either by recombinant methods or other methods known to those skilled in the art including chemical syntheses. Naturally produced IL-6 can be the expression product of a prokaryotic or eukaryotic host cell transformed or transfected with a DNA sequence encoding IL-6 or encoding a biologically active IL-6 fragment. A preferred host cell includes *E. coli*. The activated PEG used to produce PEG-IL-6 can be any of many activated PEG known to those skilled in the art including activated polyethylene glycol (4500), activated polyethylene glycol (5000), activated polyethylene glycol (12000), and the like. The particular activated PEG chosen can be any of a broad range of molecular weights as known to those skilled in the art and as used herein includes the molecular weight range of 4500 to 12000. Particularly preferred activated PEG includes the succinimidyl succinate derivatives of PEG and the bis-PEG derivatives of cyanuric chloride. The PEG can be attached to the IL-6 via one or more amino groups or one or more carboxyl groups. The number of PEG moieties per IL-6 protein, polypeptide or fragment can vary as can the molecular weight of the PEG moiety. Generally, the higher the degree of PEGylation, i.e., the greater the number of PEG groups per protein molecule, the greater the in vivo biological activity of the IL-6; similarly, the higher the molecular weight of the PEG used to PEGylate, the fewer the number of PEG groups per protein molecule required for in vivo activity. Generally, at least two, and preferably more than five PEG moieties, should be attached per IL-6 protein polypeptide, or fragment. Preferred PEG-IL-6 molecules include: PEG1IL6; PEG2IL6; PEG12MIL6; PEG(4500)IL-6, including fractions Fr45-0, Fr45-1, Fr45-2, Fr45-3, and Fr45-4; PEG(10000)IL-6, including fractions Fr100-0, Fr100-1, Fr100-2, Fr100-3, Fr100-4, and Fr100-5; PEG(12000)IL-6, including fractions Fr120-1, Fr120-2, Fr120-3, Fr120-4, and Fr120-5; and PEG(12000)IL-6', including the fractions Fr120'-1, Fr120'-2, Fr120'-3, Fr120'-4, and Fr120'-5.

The present invention also provides for a method to produce such improved IL-6 comprising chemical modification of the polypeptide. The present invention further provides for the use of such improved IL-6 for treating disorders associated with thrombocytopenia and/or impaired platelet functions. In cancer therapy, a dramatic drop in platelet count is frequently induced by the high-dose administrations of carcinostatics; this drop causes a variety of disorders such as excessive hemorrhaging. The improved IL-6 of the present invention is expected to be useful in reducing side effects associated with cancer chemotherapy. According to the method of the invention, haematopoietic disorders can be treated in an organism by administering a therapeutically effective amount of a composition comprising PEG-IL-6. The method further comprises the step of promoting platelet production. Also provided by the invention are pharmaceutical compositions for use in treatment of haematopoietic disorders in an organism; the composition comprises a pharmaceutically acceptable solvent, diluent, adjuvant or carrier and, as the active ingredient, from about 0.0001 mg to about 10 mg per kg of body weight of the afflicted organism per day of PEG-IL-6, and preferably in the range of 0.004–1 mg per kg body weight per day. Also provided is a method for treatment of haematopoietic disorders in an organism by administering the novel pharmaceutical compositions of PEG-IL-6.

Other aspects and advantages of the present invention will be apparent upon consideration of the following detailed description thereof which includes numerous illustrative examples of the practice of the invention.

DETAILED DESCRIPTION OF THE INVENTION

Described below is the chemical modification with PEG of at least one amino group of polypeptides possessing IL-6 activities. This modification results in an increase in in vivo half-life in blood and an increase of in vivo platelet producing activity as compared to that of unmodified IL-6. Thus, in one aspect of the present invention, modified glycosylated and unglycosylated proteins or polypeptides (preferably polypeptides) possessing improved interleukin-6 activities, particularly platelet producing activity, in primates, and especially in humans, are provided where the modification comprises the attachment of PEG to the polypeptides.

The attachment of PEG (hereafter referred to as PEGylation) to the molecules possessing IL-6 activities may be done via the amino or carboxyl groups present in the polypeptides, and is preferably via the amino groups. For PEGylation via amino groups, at least one hydrogen atom of an amino group of the protein or protein fragment to be PEGylated is substituted with a group as shown in formula 1 or 2:

FORMULA 1 n: a positive integer between 7 and 600.
$R_1$: an alkyl group with one to three carbons.

FORMULA 2 n, m: a positive integer between 7 and 600, and may be equal or different.

R$_1$, R$_2$: an alkyl group with one to three carbons, and may be the same or different.

In the present invention, hIL-6 polypeptides having substantially the following amino acid sequence are preferred as either the glycosylated or unglycosylated proteins or polypeptides possessing IL-6 activities:

SEQUENCE ID NO.: 1

| | | | | | | | | | | | | |
|---|---|---|---|---|---|---|---|---|---|---|---|---|
| ALA | PRO | VAL | PRO | PRO 5 | GLY | GLU | ASP | SER | LYS 10 | ASP | VAL | ALA | ALA |
| PRO 15 | HIS | ARG | GLN | PRO | LEU 20 | THR | SER | SER | GLU | ARG 25 | ILE | ASP | LYS |
| GLN | ILE 30 | ARG | TYR | ILE | LEU | ASP 35 | GLY | ILE | SER | ALA | LEU 40 | ARG | LYS |
| GLU | THR | CYS 45 | ASN | LYS | SER | ASN | MET 50 | CYS | GLU | SER | SER | LYS 55 | GLU |
| ALA | LEU | ALA | GLU 60 | ASN | ASN | LEU | ASN | LEU 65 | PRO | LYS | MET | ALA | GLU 70 |
| LYS | ASP | GLY | CYS | PHE 75 | GLN | SER | GLY | PHE | ASN 80 | GLU | GLU | THR | CYS |
| LEU 85 | VAL | LYS | ILE | ILE | THR 90 | GLY | LEU | LEU | GLU | PHE 95 | GLU | VAL | TYR |
| LEU | GLU 100 | TYR | LEU | GLN | ASN | ARG 105 | PHE | GLU | SER | SER | GLU 110 | GLU | GLN |
| ALA | ARG | ALA 115 | VAL | GLN | MET | SER | THR 120 | LYS | VAL | LEU | ILE | GLN 125 | PHE |
| LEU | GLN | LYS | LYS 130 | ALA | LYS | ASN | LEU | ASP 135 | ALA | ILE | THR | THR | PRO 140 |
| ASP | PRO | THR | THR | ASN 145 | ALA | SER | LEU | LEU | THR 150 | LYS | LEU | GLN | ALA |
| GLN 155 | ASN | GLN | TRP | LEU | GLN 160 | ASP | MET | THR | THR | HIS 165 | LEU | ILE | LEU |
| ARG | SER 170 | PHE | LYS | GLU | PHE | LEU 175 | GLN | SER | SER | LEU | ARG 180 | ALA | LEU |
| ARG | GLN | MET 185 | | | | | | | | | | | |

As used herein "substantially" means that the polypeptides may have one or more amino acid modification(s) (deletions, additions, insertions, or substitutions) of the above amino acid sequence as long as the modification(s) does not have any adverse affect on the function and biological activity of the polypeptides. Examples of such modifications are described in published patent applications EP 257406, WO 88/00206 and EP 363083 as well as in Brakenhoff, J. P. J., (*J. Immunol.,* 143:1175 (1989)).

The polypeptides may be produced by a number of methods including genetic engineering; hIL-6 polypeptides produced by recombinant *E. coli* are preferred as they can be obtained in good purity and in large quantity. A polypeptide with exactly the above amino acid sequence or the above amino acid sequence with one methionine or a Met-Lys dipeptide added at the N-terminus is especially preferred. These hIL-6 polypeptides may be produced by the procedure disclosed in PCT patent application WO 88/00206 (Genetics Institute Incorporated). They may also be produced by first chemically synthesizing a DNA sequence encoding hIL-6 polypeptides (Haegeman, G., et al., *Eur. J. Biochem.,* 159:625 (1986)) and then expressing the DNA in *E. coli* by the method of Souza et al. (WO 87/01132) (U.S. Pat. No. 4,810,643).

As used herein in the formulae, m and n indicate average values; m and n may be equal or different, are preferably equal and between 7 and 600, more preferably between 7 and 250, and most preferably between 30 and 150. The average molecular weight of the PEG used in the present invention may be between 300 and 30,000; and is preferably between 1,000 and 20,000; and is most preferably 12,000. The protecting groups for the hydroxyl group of the PEG, indicated as R$^1$ and R$^2$, may be alkyl groups, with one to three carbon atoms, such as methyl, ethyl, n-propyl or i-propyl groups, and are preferably methyl groups.

As a further aspect of the present invention there are provided processes for producing the PEGylated glycosylated proteins or polypeptides possessing IL-6 activities. The PEGylation of the amino groups on polypeptides possessing IL-6 activities (hereafter referred to as IL-6 polypeptides) may be achieved via succinimide (formula 1) or triazine (formula 2), and is preferably via succinimide. In the PEGylation via succinimide, PEG shown in formula 3 is coupled with the compound shown in formula 4 to obtain the compound shown in formula 5, which is then coupled to IL-6 polypeptides. Some of the activated PEGs, represented by the generic formula 5, are commercially available from, for example, Nippon Oil & Fats Co. (Tokyo, Japan). Formula 5 is a generic formula representative of succinimidyl succinate derivatives of PEG.

FORMULA 3

PEG n, $R_1$: same as in formula 1.

FORMULA 4

FORMULA =5

Succinimidyl Succinate Derivative of PEG n, $R_1$: same as in formula 1.

The coupling of activated PEG (formula 5) to IL-6 polypeptides may be achieved by incubating in 0.25 M sodium borate buffer (pH 8.0–8.5) for one to three hours at 4° C. The activated PEG may be added to the reaction mixture serially in small quantities to avoid its degradation. After the reaction, the PEGylated IL-6 polypeptides can be separated from unreacted materials by gel filtration and ion-exchange column chromatography.

For PEGylation via triazine, PEG shown in formula 3 is coupled with the compound shown in formula to obtain the compound shown in formula 7; the formula 6 activated PEG is then coupled to IL-6 polypeptides. Some of the compounds represented by the generic formula 7 are commercially available from, for example, Seikagaku Kogyo Co. (Tokyo, Japan).

FORMULA 6

FORMULA 7

Bis-PEG Derivative of Cyanuric Chloride n, m, $R_1$, $R_2$: same as in formula 2.

The coupling of activated PEG (formula 7) and IL-6 polypeptides may be achieved by incubating in 0.25 M sodium borate buffer (pH 10.0) for two to twenty hours at 4° C. to room temperature. The activated PEG may be added to the reaction mixture serially in small quantities to avoid its degradation. After the reaction, the PEGylated IL-6 polypeptides can be separated from unreacted materials by gel filtration and ion-exchange column chromatography.

The PEGylation of the carboxyl groups on IL-6 polypeptides may be achieved by coupling the polypeptides with the PEG shown in formula 8.

FORMULA 8 n: same as in formula 1.

As a general rule, the higher the degree of PEGylation, i.e., the greater the number of PEG groups per protein molecule, the better the in vivo activity; and, the higher the molecular weight of the PEG used to PEGylate, the fewer the number of PEG groups per protein molecule required for in vivo activity. Generally, at least 2 and preferably more than 5 PEG moieties should be attached per IL-6 protein.

As used herein, the following abbreviations and terms include, but are not necessarily limited to, the following definitions.

Activated PEG1 is a generic term used to indicate activated polyethylene glycol (4500);

Activated PEG2 is a generic term used to indicate activated polyethylene glycol (5000);

Activated PEG12M is a generic term used to indicate activated polyethylene glycol (12000);

PEG(4500)IL-6 is a generic term used to indicate the product formed upon the reaction of the succinimidyl succinate derivatives of PEG(4500) with IL-6;

PEG(10000)IL-6 is a generic term used to indicate the product formed upon the reaction of the bis-PEG (5000) derivatives of cyanuric chloride with IL-6; and PEG(12000)IL-6 is a generic term used to indicate the product formed upon the reaction of the succinimidyl succinate derivatives of PEG(12000) with IL-6.

The numbers in parentheses, i.e., 4500, 5000, and 12000 refer to the average molecular weight of polyethylene glycol.

As used herein, "haematopoietic disorders and deficiencies" include but are not limited to thrombocytopenia, granulocytopenia, and anemia.

The PEGylated IL-6 of the present invention has a much longer plasma half-life and upon administration to mice has a far superior capacity to increase the number of platelets compared to unmodified IL-6 polypeptides or glycosylated IL-6; further, the PEGylated IL-6 of the invention has very low toxicity. Thus, in another aspect of the present invention, therapeutic agents for treating haematopoietic disorders, particularly acute thrombocytopenia, and deficiencies are provided. Such agents comprise a therapeutically effective amount of the PEGylated IL-6 of the present invention in an admixture with a pharmaceutically acceptable carrier. The agents may be administered orally as tablets or capsules, or parenterally by injection. Generally, the daily dosage regimen is in the range of 0.0001-10 mg/kg weight (as polypeptide), and preferably in the range of 0.004-1 mg/kg.

The following examples illustrate practice of the invention.

Example 1 relates to the preparation of Fr45-0 from hIL-6 polypeptide and an activated PEG1 (methoxypolyethylene glycol (4500) succinimidyl succinate).

Example 2 relates to the SDS-PAGE characterization of Fr45-0.

Example 3 relates to the preparation of Fr100-0 from hIL-6 polypeptide and an activated PEG2 (bismethoxypolyethylene glycol (5000) cyanuric chloride).

Example 4 relates to the preparation of four fractions of PEGylated hIL-6 polypeptide: Fr45-1, Fr45-2, Fr45-3, and Fr45-4 from hIL-6 and the activated PEG1 of Example 1.

Example 5 relates to the SDS-PAGE characterization of the four fractions of Example 4.

Example 6 demonstrates the capacity of the four fractions obtained in Example 4 capacity to induce IgM production in a B cell leukemic cell-line.

Example 7 compares the in vivo platelet producing activity of hIL-6, Fr45-0 and Fr100-0 (as prepared in Examples 1-3).

Example 8 compares the in vivo platelet producing activity of hIL-6 and of the four fractions of Example 4.

Example 9 relates to the subcutaneous administration of hIL-6 or PEGylated hIL-6 (Fr45-2, produced in Example 4) to acute-thrombocytopenic mice following x-ray irradiation.

Example 10 relates to the subcutaneous administration of hIL-6, or PEGylated hIL-6 (Fr45-2, produced in Example 4) to acute-thrombocytopenic mice following treatment with the chemical carcinostatic cyclophosphamide.

Example 11 relates to the preparation of five fractions of PEGylated hIL-6 polypeptide, Fr100-1, Fr100-2, Fr100-3, Fr100-4, and Fr100-5, from hIL-6 and the activated PEG2 of Example 3.

Example 12 relates to the coupling of hIL-6 polypeptide to an activated PEG12M (methoxypolyethylene glycol (12000) succinimidyl succinate) and the preparation therefrom of five fractions of PEGylated hIL-6 polypeptide: Fr120-1, Fr120-2, Fr120-3, Fr120-4, and Fr120-5.

Example 13 provides the results of a study to compare the level of platelet production following the administration of the hIL-6 (produced in Example 4) or its PEGylated derivatives (produced in Examples 11 and 12).

Example 14 relates to the subcutaneous administration of PEGylated hIL-6 (produced in Example 12: Fr120-1 to Fr120-5) to acute-thrombocytopenic mice following x-ray irradiation.

Example 15 demonstrates the in vivo persistence of PEGylated hIL-6 (Fr45-2, Fr120-1, and Fr120-2 produced in Examples 4 and 12) as compared to unmodified hIL-6.

Example 16 describes the preparation of five fractions of PEGylated hIL-6: Fr120'-1 to Fr120'-5 from the hIL-6 polypeptide of Example 4 (however, without the cathepsin C treatment) and the activated PEG12M of Example 12.

Example 17 provides the results of an acute toxicity assay of the hIL-6 of Example 4 and its PEGylated derivatives Fr45-2, Fr100-2, and Fr120-2 (produced in Examples 4, 11, and 12).

In Examples 7-10 and 13-17, the PEGylated hIL-6 polypeptides of the present invention were dissolved in PBS containing 0.1% normal mouse serum. The concentration of the solutions was adjusted so that the final volume administered was 100 μl.

EXAMPLE 1

A DNA sequence encoding the hIL-6 polypeptide with the following amino acid sequence was chemically synthesized and then introduced and expressed in *E. coli* as described by Souza et al. (WO 87/01132).

SEQ ID NO.: 2

| MET | ALA | PRO | VAL | PRO | PRO | GLY | GLU | ASP | SER | LYS | ASP | VAL | ALA |
|-----|-----|-----|-----|-----|-----|-----|-----|-----|-----|-----|-----|-----|-----|
| −1 | 1 | | | | | | | | 10 | | | | |
| ALA | PRO | HIS | ARG | GLN | PRO | LEU | THR | SER | SER | GLU | ARG | ILE | ASP |
| | 15 | | | | 20 | | | | | 25 | | | |
| LYS | GLN | ILE | ARG | TYR | ILE | LEU | ASP | GLY | ILE | SER | ALA | LEU | ARG |
| | | 30 | | | | | 35 | | | | | 40 | |
| LYS | GLU | THR | CYS | ASN | LYS | SER | ASN | MET | CYS | GLU | SER | SER | LYS |
| | | | 45 | | | | | 50 | | | | | 55 |
| GLU | ALA | LEU | ALA | GLU | ASN | ASN | LEU | ASN | LEU | PRO | LYS | MET | ALA |
| | | | | 60 | | | | | 65 | | | | |
| GLU | LYS | ASP | GLY | CYS | PHE | GLN | SER | GLY | PHE | ASN | GLU | GLU | THR |
| 70 | | | | | 75 | | | | | 80 | | | |
| CYS | LEU | VAL | LYS | ILE | ILE | THR | GLY | LEU | LEU | GLU | PHE | GLU | VAL |
| | 85 | | | | | 90 | | | | | 95 | | |
| TYR | LEU | GLU | TYR | LEU | GLN | ASN | ARG | PHE | GLU | SER | SER | GLU | GLU |
| | | 100 | | | | | 105 | | | | | 110 | |

|     |     |     |     |     |     |     |     |     |     |     |     |
| --- | --- | --- | --- | --- | --- | --- | --- | --- | --- | --- | --- |
| GLN | ALA | ARG | ALA 115 | VAL | GLN | MET | SER | THR 120 | LYS | VAL | LEU | ILE | GLN 125 |
| PHE | LEU | GLN | LYS | LYS 130 | ALA | LYS | ASN | LEU | ASP 135 | ALA | ILE | THR | THR |
| PRO 140 | ASP | PRO | THR | THR | ASN 145 | ALA | SER | LEU | LEU | THR 150 | LYS | LEU | GLN |
| ALA | GLN 155 | ASN | GLN | TRP | LEU | GLN 160 | ASP | MET | THR | THR | HIS 165 | LEU | ILE |
| LEU | ARG | SER 170 | PHE | LYS | GLU | PHE | LEU 175 | GLN | SER | SER | LEU | ARG 180 | ALA |
| LEU | ARG | GLN | MET 185 |

*E. coli* cells (300 g), that accumulated hIL-6 polypeptide, were harvested by centrifugation for 10 min at 3500 g. The hIL-6 polypeptide was extracted, solubilized and re-folded as described in EP 257406. Approximately 2.9 g of the hIL-6 polypeptide, which was a single band on SDS-PAGE and had the predicted molecular weight of 21K, was obtained.

An activated PEG1 (a succinimidyl succinate derivative of polyethylene glycol, which is methoxypolyethylene glycol succinate with an average molecular weight of 4500 and coupled to N-hydroxysuccinimide) was commercially obtained from Nippon Oil & Fats Co. (Tokyo, Japan).

The hIL-6 polypeptide (200 μg) was incubated with 1.5 mg of the activated PEG1 in 370 μl of 0.25 M sodium borate buffer (pH 8.5) for two hours at 4° C. The reaction was stopped by lowering the pH by adding 2 N hydrochloric acid. The molar ratio of the activated PEG to the free amino groups on the IL-6 polypeptide was approximately two to one. The reaction mixture was applied to a gel filtration column equilibrated with phosphate buffered saline (PBS) to exchange the buffer and was then subjected to the separation procedure below.

The buffer-exchanged solution (3.5 ml) was applied to an HPLC gel-filtration column filled with TSK-gel G3000SW (Toso Co., Tokyo, Japan). The PEGylated hIL-6 polypeptide, having one to three PEG moieties per molecule, was eluted in the first peak to give a yield of approximately 20 μg. The PEGylated hIL-6 polypeptide so obtained was termed Fr45-0.

EXAMPLE 2

The Fr45-0 obtained in Example 1 was characterized by SDS-PAGE (Fast System, Pharmacia; 10–15% gradient gel). The polypeptides were stained with silver staining and the molecular weights were estimated by comparison with standard molecular weight markers (Bio-Rad, Richmond, Ca.). The apparent molecular weights of Fr45-0 were 23K, 37K, and 50K.

EXAMPLE 3

An activated PEG2 (an activated polyethylene glycol with an average molecular weight of 10,000; synthesized by coupling two polyethylene glycol (average molecular weight 5,000) monomethylether molecules with cyanuric chloride) was commercially obtained from Seikagaku Kogyo Co., Tokyo, Japan.

The hIL-6 polypeptide (200 μg) obtained in Example 1 was incubated with 3.5 mg of the activated PEG2 in 370 μl of 0.25 M sodium borate buffer (pH 10.0) for two hours at room temperature. The reaction was stopped by lowering the pH by adding 2 N hydrochloric acid. The molar ratio of the activated PEG to the free amino groups on the IL-6 polypeptide was approximately two to one. The reaction mixture was applied to a gel filtration column equilibrated with PBS to exchange the buffer and then subjected to the separation procedure described in Example 1. The PEGylated hIL-6 polypeptide with one to two PEG moieties per molecule was eluted in the first peak to give a yield of approximately 20 μg. The PEGylated hIL-6 polypeptide so obtained was termed Fr100-0.

The apparent molecular weights of Fr100-0 were determined to be 28K and 42K as described in Example 2.

EXAMPLE 4

A DNA sequence encoding the hIL-6 polypeptide with the following amino acid sequence was chemically synthesized and then introduced and expressed in *E. coli* as described by Souza et al. (WO 87/01132).

SEQ ID NO. 3

|     |     |     |     |     |     |     |     |     |     |     |     |     |
| --- | --- | --- | --- | --- | --- | --- | --- | --- | --- | --- | --- | --- |
| MET −2 | LYS −1 | ALA 1 | PRO | VAL | PRO 5 | PRO | GLY | GLU | ASP | SER | LYS 10 | ASP | VAL |
| ALA | ALA | PRO 15 | HIS | ARG | GLN | PRO | LEU 20 | THR | SER | SER | GLU | ARG 25 | ILE |
| ASP | LYS | GLN | ILE 30 | ARG | TYR | ILE | LEU | ASP 35 | GLY | ILE | SER | ALA | LEU 40 |
| ARG | LYS | GLU | THR | CYS 45 | ASN | LYS | SER | ASN | MET 50 | CYS | GLU | SER | SER |
| LYS 55 | GLU | ALA | LEU | ALA | GLU 60 | ASN | ASN | LEU | ASN | LEU 65 | PRO | LYS | MET |

-continued

| | | | | | | | | | | | |
|---|---|---|---|---|---|---|---|---|---|---|---|
| ALA | GLU 70 | LYS | ASP | GLY | CYS | PHE 75 | GLN | SER | GLY | PHE | ASN 80 | GLU | GLU |
| THR | CYS | LEU 85 | VAL | LYS | ILE | ILE | THR 90 | GLY | LEU | LEU | GLU | PHE 95 | GLU |
| VAL | TYR | LEU | GLU 100 | TYR | LEU | GLN | ASN | ARG 105 | PHE | GLU | SER | SER | GLU 110 |
| GLU | GLN | ALA | ARG | ALA 115 | VAL | GLN | MET | SER | THR 120 | LYS | VAL | LEU | ILE |
| GLN PHE 125 | LEU | GLN | LYS | LYS 130 | ALA | LYS | ASN | LEU | ASP 135 | ALA | ILE | THR |
| THR | PRO 140 | ASP | PRO | THR | THR | ASN 145 | ALA | SER | LEU | LEU | THR 150 | LYS | LEU |
| GLN | ALA | GLN 155 | ASN | GLN | TRP | LEU | GLN 160 | ASP | MET | THR | THR | HIS 165 | LEU |
| ILE | LEU | ARG | SER 170 | PHE | LYS | GLU | PHE | LEU 175 | GLN | SER | SER | LEU | ARG 180 |
| ALA | LEU | ARG | GLN | MET 185 | | | | | | | | | |

This amino acid sequence has N-terminal residues of Met-Lys-Ala-Pro-and thus can be conveniently converted to Ala-Pro-, the natural hIL-6 sequence, by cleaving off the Met-Lys using cathepsin C.

*E. coli* cells (300 g), that had accumulated hIL-6 polypeptide, were harvested by centrifugation for 10 min at 3500 g, and the hIL-6 polypeptide was extracted, solubilized and refolded as described in EP 257406. After changing the buffer to 20 mM sodium acetate buffer, the polypeptide was treated with 6 U of cathepsin C (Boeringer Mannheim GmBH, Mannheim, Germany) for one hour at room temperature. The reaction mixture was quick-chilled and sodium phosphate buffer (pH 6.0) was added to a final concentration of 2 mM. The mixture was applied to a hydroxyapatite column equilibrated with 2 mM sodium phosphate buffer (1300 mmho, pH 6.0), and the hIL-6 was eluted in a peak fraction of 1200 ml with the same buffer. This fraction was then applied to a CM-Sepharose TM column equilibrated with 20 mM sodium acetate buffer (pH 6.0). The column was washed with the same buffer, and the hIL-6 was eluted in a peak fraction of 580 ml with a linear gradient of 0–0.3 M NaCl in the same buffer.

Approximately 1.5 g of the hIL-6 polypeptide, which was a single band on SDS-PAGE and had the predicted molecular weight of 21K, was obtained. The N-terminal sequence was confirmed to be Ala-Pro-Val-Pro-by direct sequence analysis.

The hIL-6 polypeptide (100 mg) was dissolved in 100 ml of 0.1 M sodium borate buffer (pH 8.5) and 1125 mg of the activated PEG1 of Example 1 was added to the solution in an ice bath with stirring. The activated PEG1 was added either all at one time or in five additions at 30 min intervals, and the latter was found to give a better yield of the coupled product. Accordingly, the subsequent purification steps were carried out on the reaction mixture to which the activated PEG1 was added in five separate, sequential additions.

The reaction mixture was concentrated to 10 ml using YM10 ultrafiltration membrane (Amicon, Danvers, Ma.) and was applied to a Sephadex TM G100 column equilibrated with 20 mM sodium acetate buffer (pH 6.0). The PEGylated hIL-6 polypeptide was eluted in four fractions (hereafter referred to as Fr45-1, Fr45-2, Fr45-3, Fr45-4) with the same acetate buffer. Upon SDS-PAGE analysis, each fraction gave a main band of 91K, 68K, 41K, and 26K; respectively. The yield of each fraction was 2.9 mg, 4.0 mg, 2.9 mg, and 2.5 mg; respectively.

EXAMPLE 5

The four fractions obtained in Example 4 were characterized by determining the number of free amino groups and by SDS-PAGE analysis.

The number of free amino groups was determined by the method of Stocks et al. (*Anal. Biochem.*, 154:232 (1986)). The PEGylated polypeptides were reacted with 7.5% fluorescamine in 0.1 M sodium phosphate (pH 8.0), and the number of free amino groups was determined by measuring the intensity of fluorescence at 475 nm (excited at 390 nm).

SDS-PAGE analysis was carried out on a 10–20% gradient gel (Daiichi-Pure Chemicals Co., Tokyo, Japan). The polypeptides were stained with CBB and the molecular weights were estimated by comparison with standard molecular weight markers (Pharmacia TM, Upsala, Sweden). Each band was quantified using an image analysis system (Immunomedica model TIF-64). The results are shown in Table 1, below.

TABLE 1

| | Molecular weight distribution (%) | | | | | # of free NH$_2$[b] |
|---|---|---|---|---|---|---|
| | 21K[a] | 26K | 41K | 68K | >91K | |
| Fr45-1 | | | | 23.0 | 77.0 | 6.1 |
| Fr45-2 | | | 14.0 | 52.2 | 33.8 | 6.8 |
| Fr45-3 | | 12.0 | 56.4 | 28.2 | 3.4 | 9.3 |
| Fr45-4 | 9.9 | 75.7 | 14.4 | | | 12.6 |

[a]Unmodified hIL-6.
[b]Average number of free amino groups per molecule (cf. hIL-6 has 15 amino groups per molecule.)

EXAMPLE 6

The four fractions obtained in Example 4 were tested for their capacity to induce IgM production in a B cell leukemic cell line SKW6-CL4 (Hirano, T., et al., *Proc. Natl. Acad. Sci. USA*, 82:5490 (1985)). The PEGylated hIL-6 polypeptides were dissolved in RPMI1640 medium containing 10% fetal calf serum. The concentration of the solution was adjusted so that the final volume of the solution added to reaction mixtures (200 μl) was 50 μl. The results are shown in Table 2. The PEGylated hIL-6 retained its activity to induce IgM production in SKW6-CL4.

TABLE 2

| Dose(pg/ml)$^a$ | IgM Production (ng/ml) | | | | |
|---|---|---|---|---|---|
| | unmodified | PEGylated hIL-6 | | | |
| | hIL-6 | Fr45-1 | Fr45-2 | Fr45-3 | Fr45-4 |
| 3750.0 | 910 | 250 | 335 | 175 | 200 |
| 937.5 | 890 | 120 | 162 | 118 | 175 |
| 58.5 | 545 | 82 | 78 | 70 | 90 |
| 7.5 | 120 | 72 | 73 | 70 | 75 |

$^a$On the basis of hIL-6 polypeptides.

EXAMPLE 7

The in vivo platelet producing activity of the hIL-6, Fr45-0, and Fr100-0, produced in Examples 1 and 3, was examined in mice. Either hIL-6, Fr45-0, Fr100-0, or the mixture of hIL-6 and PEG(4500) (in vehicle) was administered subcutaneously to three Balb/c mice (8 weeks old, female) at a dose of 10 μg/mouse (on the basis of polypeptide) once a day for five days. Control mice were administered only vehicle comprising PBS containing 0.1% normal mouse serum. Blood samples were taken on the sixth day and platelets in peripheral blood were counted. The results are shown in Table 3.

Fr45-0 and Fr100-0 induced an approximately 230% increase in the number of platelets produced, while unmodified hIL-6, or the mixture of hIL-6 and PEG(4500) induced only an approximately 150% increase.

TABLE 3

| | Number of platelets$^a$ | % |
|---|---|---|
| Vehicle | 74.5 | (100%) |
| Fr45-0 | 173.5 | (233%) |
| Fr100-0 | 170.0 | (228%) |
| hIL-6 + PEG(4500) | 117.9 | (158%) |
| hIL-6 | 113.5 | (152%) |

$^a \times 10^4/\mu l$, numbers in parentheses are % of the vehicle control.

EXAMPLE 8

The hIL-6 or its PEGylated derivatives (Fr45-1 to Fr45-4), produced in Example 4, were administered subcutaneously to four Balb/c mice (8 weeks old, female) once a day for five days. Control mice were administered only vehicle comprising PBS containing 0.1% normal mouse serum. Blood samples were taken on the sixth day and platelets in peripheral blood were counted. The results are shown in Table 4. The results also demonstrate a positive dose response relationship.

The PEGylated hIL-6 showed significantly higher platelet producing activity compared to the unmodified hIL-6.

TABLE 4

| Dose$^a$ | Number of platelets (% of control) | | | | |
|---|---|---|---|---|---|
| | unmodified | PEGylated hIL-6 | | | |
| | hIL-6 | Fr45-1 | Fr45-2 | Fr45-3 | Fr45-4 |
| 10 | 126.6** | 250.9*** | 214.4* | 194.0** | 173.5** |
| 5 | 130.2* | 224.6*** | 188.9*** | 188.9*** | 144.2* |
| 1 | 111.1 | 143.6* | 151.5* | 128.8* | 124.0 |
| 0.5 | 115.8 | 135.4** | 125.8** | 134.4** | 107.2 |
| 0.1 | 100.4 | 103.2 | 102.0 | 92.8 | 107.6 |

$^a$μg/mouse/injection on the basis of hIL-6 polypeptides.
*P < 0.05, P < 0.01, *P < 0.001 significant difference from the control (Student's T-test).

EXAMPLE 9

Figure 1:
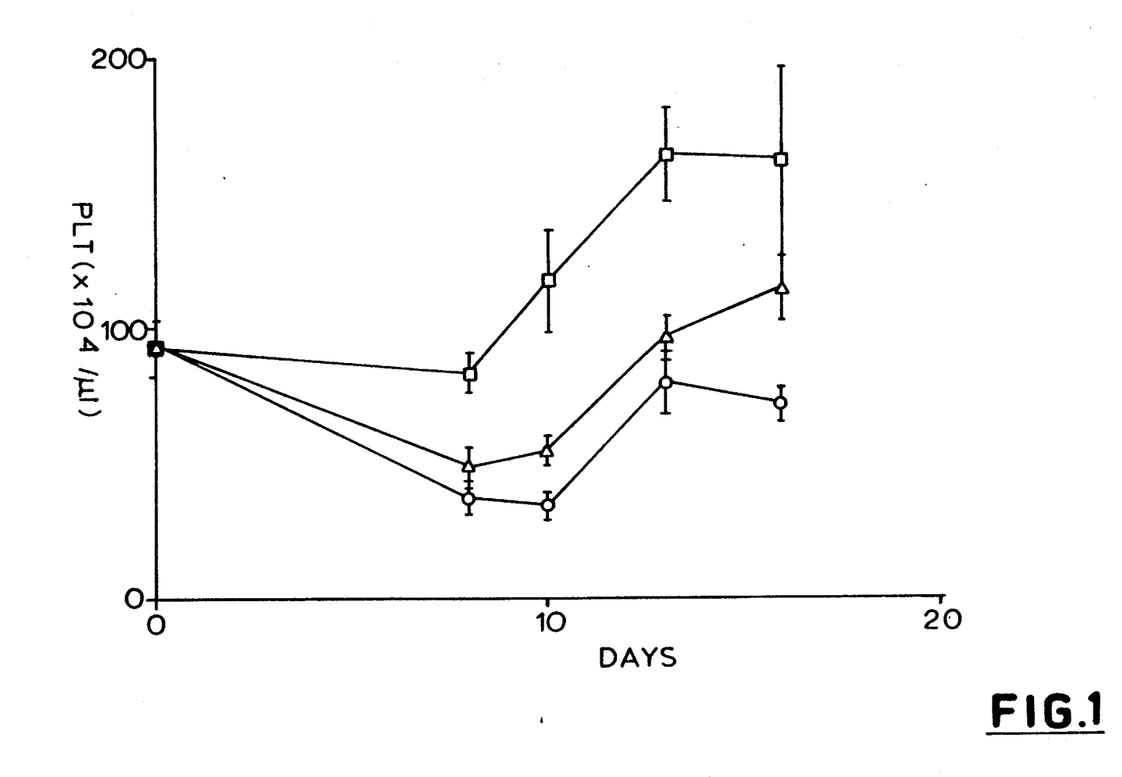
FIG. 1 is a graph showing the effect of the administration of modified (Fr45-2) and unmodified hIL-6 on the number of peripheral platelets present after X-ray irradiation of mice.

The hIL-6 or its PEGylated derivative (Fr45-2), produced in Example 4, was administered subcutaneously to four acutely thrombocytopenic mice once a day at a dose of 5 μg/mouse for 10 serial days following X-ray irradiation (600 rad). Blood samples were taken daily and platelets in peripheral blood were counted. The results are shown in FIG. 1 wherein circles, squares and triangles respectively represent data points obtained for Fr45-2 and for IL-6.

PEGylated hIL-6 administration resulted in at least five days earlier recovery from the thrombocytopenia than the control vehicle administration, while unmodified hIL-6 administration resulted in one to two days earlier recovery.

In another test, five X-ray irradiated mice were administered hIL-6 or the Fr45-2 once a day for 7 serial days at a dose of 5 or 50 μg/mouse as described above. Blood samples were taken on the eighth day when the acute decrease of platelets in vehicle administered mice reached the minimum, as is seen in FIG. 1, and platelets in peripheral blood were counted. The results are shown in Table 5.

The 5 μg/mouse administration of the Fr45-2 completely prevented the acute drop in the platelet number while even 50 μg/mouse administration of the unmodified hIL-6 did not result in significant recovery from the acute thrombocytopenia.

TABLE 5

| | Number of platelets$^a$ | % |
|---|---|---|
| Vehicle | 40.8 | (63) |
| Fr45-2 (5 μg) | 83.0 | (127) |
| hIL-6 (5 μg) | 47.0 | (72) |
| hIL-6 (50 μg) | 53.1 | (82) |
| Normal$^b$ | 65.1 | (100) |

$^a \times 10^4/\mu l$, (numbers in parentheses are % of the non-irradiated control)
$^b$Not irradiated with X-ray.

EXAMPLE 10

Figure 2:
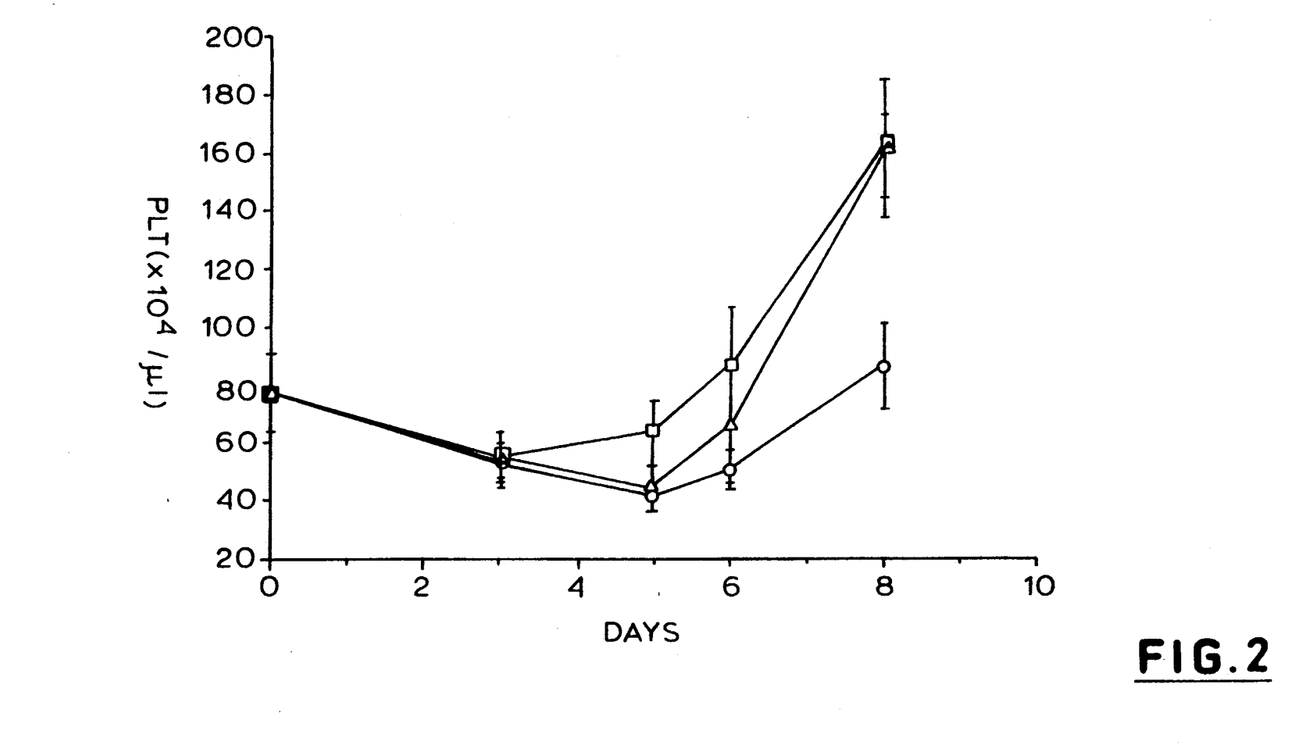
FIG. 2 is a graph showing the effect of the administration of modified (Fr45-2) and unmodified hIL-6 on the number of peripheral platelets after chemical carcinostatic treatment of mice.

The hIL-6 or its PEGylated derivative (Fr45-2), produced in Example 4, was administered subcutaneously to four acute-thrombocytopenic mice, that had been treated with 200 mg/kg of a chemical carcinostatic cyclophosphamide (CY), once a day at a dose of 5 μg/mouse for hIL-6 and 1 μg/mouse for PEGylated hIL-6 for 7 serial days following the CY administration. Blood samples were taken daily and platelets in peripheral blood were counted. The results are shown in FIG. 2 wherein circles, squares and triangles respectively represent data points obtained for the vehicle along, for Fr45-2 and for hIL-6.

PEGylated hIL-6 administration resulted in significantly earlier recovery from the thrombocytopenia than the control vehicle administration, while unmodified hIL-6 administration induced platelet increase but not early recovery.

EXAMPLE 11

As described below, the hIL-6 polypeptide produced in Example 4 was coupled to the activated PEG2 of Example 3.

The hIL-6 polypeptide (100 mg) was dissolved in 200 ml of 0.1 M sodium borate buffer (pH 10.0) and 2500 mg of the activated PEG2 was added to the solution in five additions at 30 min intervals at room temperature with stirring. The reaction mixture was concentrated to 8 ml using YM10 ultrafiltration membrane (Amicon, Danvers, Ma.) to give a PEG(10000)IL-6 and 3.5 ml of the concentrate was applied to a Superdex G200 ™ column (Pharmacia ™, Upsala, Sweden) equilibrated with PBS. The PEGylated hIL-6 polypeptide was eluted in five fractions (hereafter referred to as Fr100-1, Fr100-2, Fr100-3, Fr100-4, Fr100-5) with PBS. The yield of each fraction was 3.8 mg, 5.9 mg, 5.8 mg, 4.8 mq, and 4.5 mg; respectively.

The five fractions obtained were characterized by determining the number of free amino acid groups as described in Example 5. The average number of free amino groups per molecule of each fraction was 5.3, 7.4, 8.6, 9.4, and 10.0; respectively.

EXAMPLE 12

An activated PEG12M (a succinimidyl succinate derivative of polyethylene glycol, which is methoxypolyethylene glycol succinate with an average molecular weight of 12,000 and coupled to N-hydroxysuccinimide) was obtained from Nippon Oil & Fats Co. (Tokyo, Japan). The hIL-6 polypeptide produced in Example 4 was coupled to this activated PEG12M.

The hIL-6 polypeptide (90 mg) was dissolved in 180 ml of 0.1 M sodium borate buffer (pH 8.5) and 1000 mg of the activated PEG12M was added to the solution in three additions at 30 min intervals in an ice bath with stirring. The reaction mixture was concentrated to 6 ml using YM10 ultrafiltration membrane (Amicon ™) to give a PEG(12000)IL-6 and was applied to a Superdex G200 ™ column (Pharmacia ™) equilibrated with PBS. The PEGylated hIL-6 polypeptide was eluted in five fractions (hereafter referred to as Fr120-1, Fr120-2, Fr120-3, Fr120-4, Fr120-5) with PBS. The yield of each fraction was 1.6 mg, 2.8 mg, 3.5 mg, 3.7 mg, and 3.7 mg; respectively.

The five fractions obtained were characterized by determining the number of free amino acid groups as described in Example 5. The average number of free amino groups per molecule of each fraction was 5.2, 7.6, 8.7, 9.2, and 9.8; respectively.

EXAMPLE 13

The hIL-6 produced in Example 4 or its PEGylated derivatives produced in Examples 11 and 12 were administered subcutaneously to four Balb/c mice (8 weeks old, female) once a day for five days. Control mice were administered with the vehicle. Blood samples were taken on the sixth day and platelets in peripheral blood were counted. The results are shown in Tables 6 and 7.

The PEGylated hIL-6 showed significantly higher platelet producing activity compared to the unmodified hIL-6. Generally, the PEGylated hIL-6 derivatives of Example 12 gave higher activity.

TABLE 6

| Dose[a] | Number of platelets (% of control) | | | | | |
|---|---|---|---|---|---|---|
| | unmodified hIL-6 | PEGylated hIL-6 [Example 11] | | | | |
| | | Fr100-1 | Fr100-2 | Fr100-3 | Fr100-4 | Fr100-5 |
| 10 | 143.0*** | 211.1*** | 250.8*** | 204.4*** | 203.2*** | 202.4** |
| 5 | 129.4** | nt | 205.9*** | 212.7*** | 226.5** | 225.9** |
| 1 | nt | 100.0 | 148.9** | 141.1** | 142.5* | 142.8* |
| 0.5 | nt | nt | 107.9 | 113.7 | 138.7** | 111.3 |

[a] μg/mouse/injection on the basis of hIL-6 polypeptides.
nt: not tested.
*P < 0.05, P < 0.01, *P < 0.001 significant difference from the control (Student's T-test).

TABLE 7

| Dose[a] | Number of platelets (% of control) | | | | | |
|---|---|---|---|---|---|---|
| | unmodified hIL-6 | PEGylated hIL-6 [Example 12] | | | | |
| | | Fr120-1 | Fr120-2 | Fr120-3 | Fr120-4 | Fr120-5 |
| 10 | 126.7* | 201.3* | 213.2*** | 221.4*** | 200.4*** | 235.9*** |
| 5 | nt | 246.3*** | 244.3*** | 243.1*** | 229.0*** | 224.8** |
| 1 | nt | 221.5** | 233.2*** | 242.7*** | 221.4** | 225.4** |
| 0.5 | nt | 215.5*** | 227.8*** | 205.9*** | 203.4*** | 191.5*** |
| 0.1 | nt | 141.3** | 167.4*** | 170.1*** | 161.5*** | 154.1*** |

[a] μg/mouse/injection on the basis of hIL-6 polypeptides.
nt: not tested.
*P < 0.05, P < 0.01, *P < 0.001 significant difference from the control (Student's T-test).

EXAMPLE 14

Figure 3:
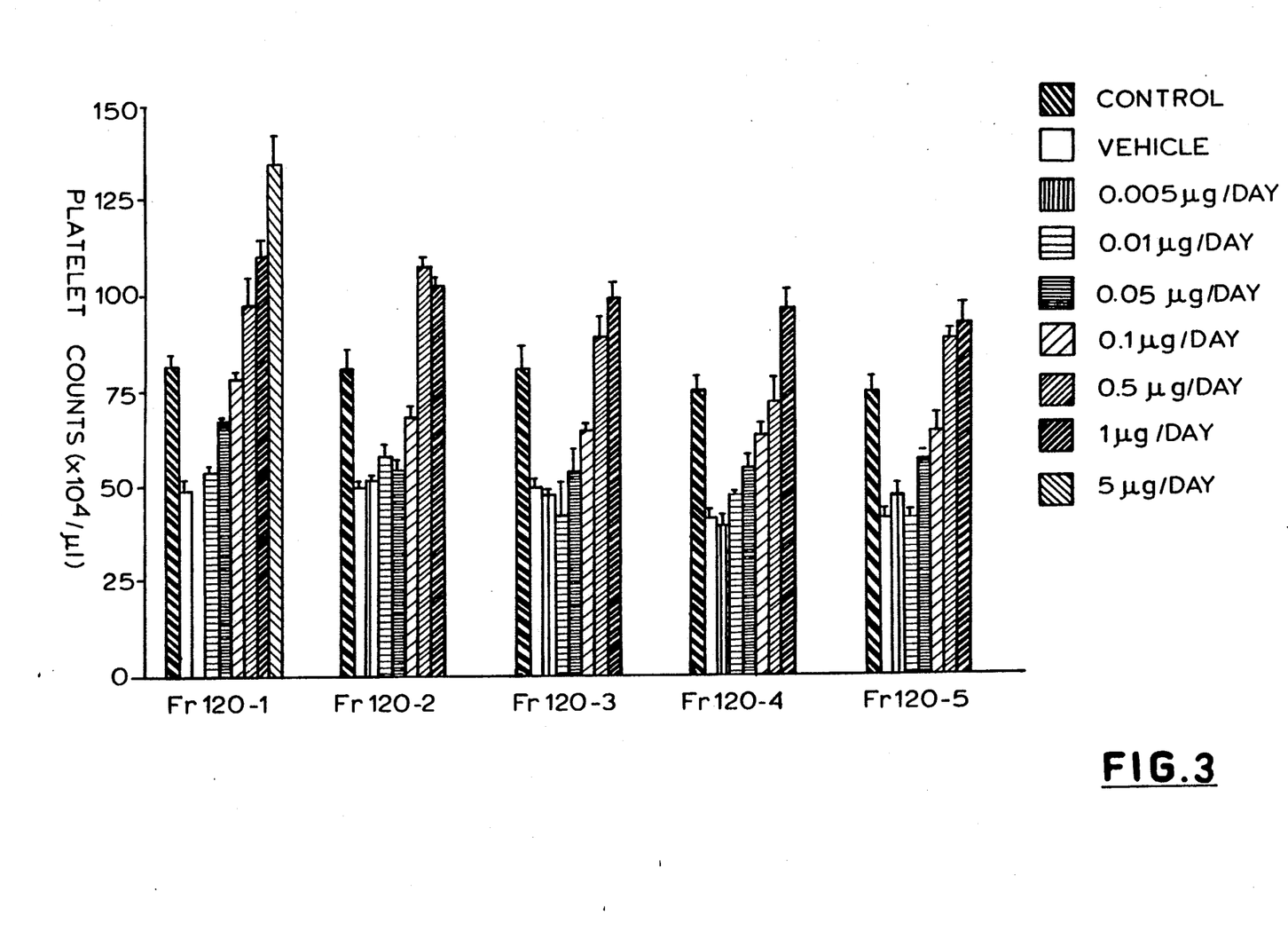
FIG. 3 is a graph showing the effect of the administration of modified (Fr120-1 to 120-5) hIL-6 administration on the number of peripheral platelets after X-ray irradiation of mice.

The PEGylated hIL-6 produced in Example 12 (Fr120-1 to Fr120-5) were administered subcutaneously to five acute-thrombocytopenic mice (8 weeks old( female), once a day for 7 serial days following X-ray irradiation (600 rad). Blood samples were taken on the eighth day and platelets in peripheral blood were counted. The results are shown in FIG. 3.

All the PEGylated hIL-6 fractions induced prominent recovery from the acute thrombocytopenia. At doses of over 0.1 μg/mouse, the administration of any of the five fractions resulted in a significantly (P<0.01) higher number of platelets produced as compared to the control (vehicle administration only). Fr120-1 and Fr120-2 were chosen for further study.

EXAMPLE 15

Figure 4:
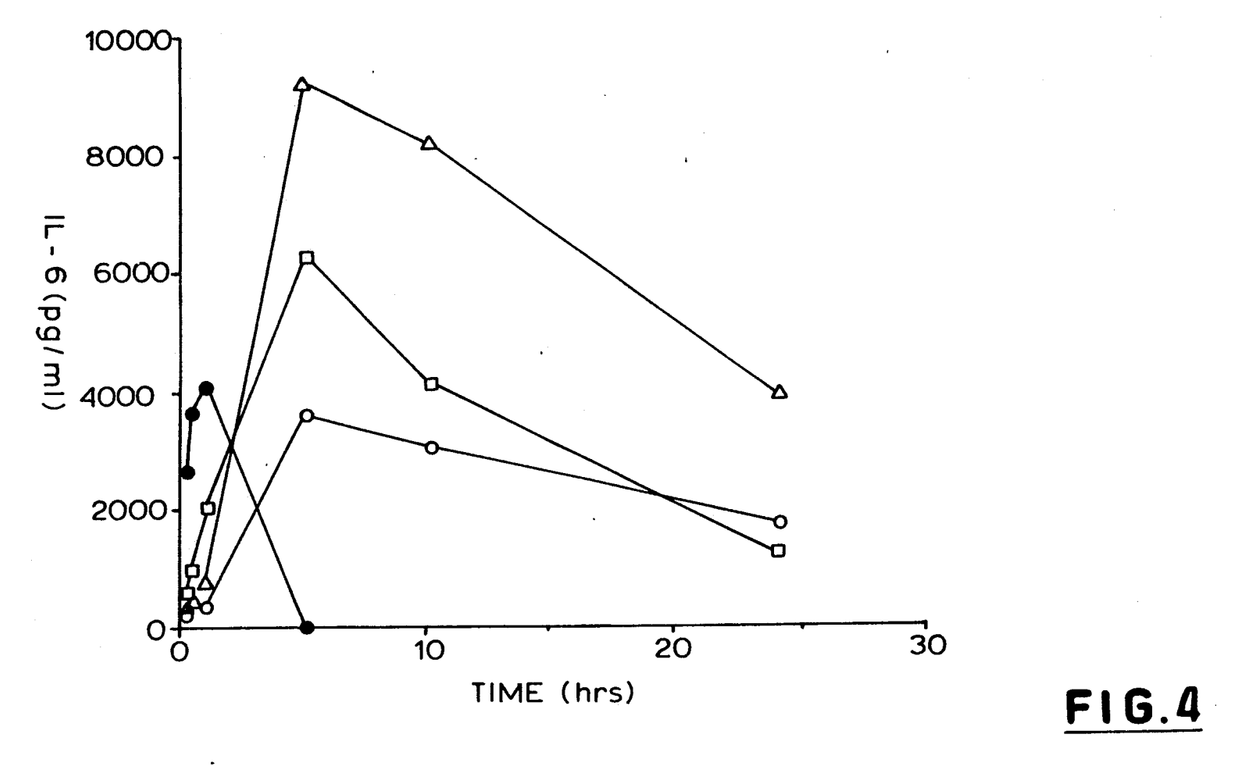
FIG. 4 is a graph showing the in vivo persistence of modified and unmodified hIL-6 in mouse blood.

The in vivo persistence of the PEGylated hIL-6 in blood was investigated. The hIL-6 of Example 4 or its PEGylated derivatives (Fr45-2, Fr120-1, and Fr120-2, produced in Examples 4 and 12) were administered subcutaneously to Balb/c mice (8 weeks old, female) at a dose of 0.2 μg/mouse (as polypeptide). Blood samples were taken at intervals and the serum concentration of hIL-6 was determined immunochemically using Quantikine hIL-6 (R&D Systems, Minneapolis, Mn.). The result is shown in FIG. 4 wherein squares, open circles, triangles and filled circles respectively represent data points obtained for Fr45-2, for Fr120-1, for Fr120-2 and for hIL-6.

The PEGylated hIL-6 could be immunochemically detected even 24 hours after the administration while the unmodified hIL-6 could not be detected 5 hours after administration. This strongly suggests that the half-life of hIL-6 was increased by PEGylation.

EXAMPLE 16

The hIL-6 polypeptide, with exactly the sequence shown in Example 4, was produced as described in Example 4 but without the cathepsin C treatment. Thus, this IL-6 has a Met-Lys at the amino terminus. Approximately 2.9 g of the hIL-6 polypeptide, which was a single band on SDS-PAGE and had the predicted molecular weight of 21K, was obtained. The N-terminal sequence was confirmed to be Met-Lys-Ala-Pro- with more than 99% purity by direct sequence analysis. This sequence was stable for at least for 4 months when stored at 4° C.

The hIL-6 polypeptide was PEGylated with the activated PEG12M of Example 12 to give a PEG(12000)IL-6 termed PEG(12000)IL-6', The five fractions obtained were termed as Fr120'-1 to Fr120'-5.

The PEGylated hIL-6 Fr120'-2 was administered to five mice once a day for five days at a dose of 1 μg/mouse and blood samples were taken on the sixth day as described in Example 13. The number of peripheral platelets in the test mice showed a 285% increase (significant at $P<0.001$) compared to the control (vehicle administered) mice.

EXAMPLE 17

The acute toxicity of PEGylated hIL-6 was investigated. The hIL-6 of Example 4 or its PEGylated derivatives (Fr45-2, Fr100-2, and Fr120-2), produced in Examples 4, 11, and 12, were administered subcutaneously to five Balb/c mice (6 weeks old, male, 21–23 g weight) at a dose of either 1, 5, or 10 mg/kg weight (as polypeptide). None of the mice was observed to die during the ten day period after the administration. Thus the acute LD50 for the three PEGylated hIL-6 was over 10 mg/kg weight.

The foregoing examples describe the PEGylation of IL-6 which substantially increases the biological half-life of IL-6 while still retaining the biological activity of IL-6.

While the present invention has been described in terms of specific methods and compositions, it is understood that variations and modifications will occur to those skilled in the art upon consideration of the present invention. For example, it is anticipated that smaller protein fragments and peptides derived from any form of IL-6, whether glycosylated or unglycosylated, and that still retain IL-6 biological activity, would also be effective in their PEGylated forms. It is also anticipated that forms of PEG other than the succinimidyl succinate derivatives of PEG (formula 5), the bispolyethylene glycol derivatives of cyanuric chloride (formula 7) and the polyoxyethylene diamines (formula 8), such as carbonyl dimidazole, phenylcarbonate, succinimidyl carbonate or maleimide derivatives of PEG and monopolyethylene glycol derivatives of cyanuric chloride, as well as other polyoxyethylene derivatives such as polyoxyethylene monoamines, will also be effective as PEGylating agents.

Although the preferred forms of PEGylated IL-6 are unglycosylated hIL-6 polypeptides PEGylated at amino groups with polyethylene glycol succinate, it is not intended to preclude other combinations of PEG and IL-6 that are effective in having improved biological half-life and in retaining IL-6 activity.

Further, it is anticipated that the general method of the invention of preparing PEGylated forms of IL-6 can be used to prepare PEGylated forms of other proteins for which it is desired to improve the biological half-life while still retaining and/or enhancing biological activity. Such other proteins include interleukin-2, interleukin-3, G-CSF, adenosine deaminase, asparaginase, urokinase and superoxide dismutase.

Numerous modifications and variations in the invention as described in the above illustrative examples are expected to occur to those skilled in the art and consequently only such limitations as appear in the appended claims should be placed thereon.

Accordingly, it is intended in the appended claims to cover all such equivalent variations which come within the scope of the invention as claimed.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 185
    ( B ) TYPE: Amino acid
    ( C ) STRANDEDNESS:
    ( D ) TOPOLOGY: Linear ( x i ) SEQUENCE DESCRIPTION: SEQ. ID. NO::1:

```
ALA  PRO  VAL  PRO  PRO  GLY  GLU  ASP  SER  LYS  ASP  VAL  ALA  ALA
          5                    10
PRO  HIS  ARG  GLN  PRO  LEU  THR  SER  SER  GLU  ARG  ILE  ASP  LYS
         15                    20                        25
```

|     |     |     |     |     |     |     |     |     |     |     |     |
|-----|-----|-----|-----|-----|-----|-----|-----|-----|-----|-----|-----|
| GLN<br>30 | ILE | ARG | TYR | ILE | LEU<br>35 | ASP | GLY | ILE | SER | ALA<br>40 | LEU | ARG | LYS |
| GLU<br>45 | THR | CYS | ASN | LYS | SER<br>50 | ASN | MET | CYS | GLU | SER<br>55 | SER | LYS | GLU |
| ALA<br>60 | LEU | ALA | GLU | ASN | ASN<br>65 | LEU | ASN | LEU | PRO | LYS<br>70 | MET | ALA | GLU |
| LYS<br>75 | ASP | GLY | CYS | PHE | GLN<br>80 | SER | GLY | PHE | ASN | GLU<br>85 | GLU | THR | CYS |
| LEU<br>85 | VAL | LYS | ILE | ILE | THR<br>90 | GLY | LEU | LEU | GLU | PHE<br>95 | GLU | VAL | TYR |
| LEU<br>100 | GLU | TYR | LEU | GLN | ASN<br>105 | ARG | PHE | GLU | SER | SER<br>110 | GLU | GLU | GLN |
| ALA<br>115 | ARG | ALA | VAL | GLN | MET<br>120 | SER | THR | LYS | VAL | LEU<br>125 | ILE | GLN | PHE |
| LEU<br>130 | GLN | LYS | LYS | ALA | LYS<br>135 | ASN | LEU | ASP | ALA | ILE<br>140 | THR | THR | PRO |
| ASP<br>145 | PRO | THR | THR | ASN | ALA<br>150 | SER | LEU | LEU | THR | LYS | LEU | GLN | ALA |
| GLN<br>155 | ASN | GLN | TRP | LEU | GLN<br>160 | ASP | MET | THR | THR | HIS<br>165 | LEU | ILE | LEU |
| ARG<br>170 | SER | PHE | LYS | GLU | PHE<br>175 | LEU | GLN | SER | SER | LEU<br>180 | ARG | ALA | LEU |
| ARG<br>185 | GLN | MET |     |     |     |     |     |     |     |     |     |     |     |

( 2 ) INFORMATION FOR SEQ ID NO:2:

( i ) SEQUENCE CHARACTERISTICS:
        ( A ) LENGTH: 186
        ( B ) TYPE: Amino acid
        ( C ) STRANDEDNESS:
        ( D ) TOPOLOGY: Linear     ( x i ) SEQUENCE DESCRIPTION: SEQ. ID. NO::2:

|     |     |     |     |     |     |     |     |     |     |     |     |     |
|-----|-----|-----|-----|-----|-----|-----|-----|-----|-----|-----|-----|-----|
| MET<br>-1 | ALA<br>1 | PRO | VAL | PRO | PRO<br>5 | GLY | GLU | ASP | SER | LYS<br>10 | ASP | VAL | ALA |
| ALA<br>15 | PRO | HIS | ARG | GLN | PRO<br>20 | LEU | THR | SER | SER | GLU<br>25 | ARG | ILE | ASP |
| LYS<br>30 | GLN | ILE | ARG | TYR | ILE<br>35 | LEU | ASP | GLY | ILE | SER<br>40 | ALA | LEU | ARG |
| LYS<br>45 | GLU | THR | CYS | ASN | LYS<br>50 | SER | ASN | MET | CYS | GLU<br>55 | SER | SER | LYS |
| GLU<br>60 | ALA | LEU | ALA | GLU | ASN<br>65 | ASN | LEU | ASN | LEU | PRO<br>70 | LYS | MET | ALA |
| GLU<br>70 | LYS | ASP | GLY | CYS | PHE<br>75 | GLN | SER | GLY | PHE | ASN<br>80 | GLU | GLU | THR |
| CYS<br>85 | LEU | VAL | LYS | ILE | ILE<br>90 | THR | GLY | LEU | LEU | GLU<br>95 | PHE | GLU | VAL |
| TYR<br>100 | LEU | GLU | TYR | LEU | GLN<br>105 | ASN | ARG | PHE | GLU | SER<br>110 | SER | GLU | GLU |
| GLN<br>115 | ALA | ARG | ALA | VAL | GLN<br>120 | MET | SER | THR | LYS | VAL<br>125 | LEU | ILE | GLN |
| PHE<br>130 | LEU | GLN | LYS | LYS | ALA<br>135 | LYS | ASN | LEU | ASP | ALA | ILE | THR | THR |
| PRO<br>140 | ASP | PRO | THR | THR | ASN<br>145 | ALA | SER | LEU | LEU | THR<br>150 | LYS | LEU | GLN |
| ALA<br>155 | GLN | ASN | GLN | TRP | LEU<br>160 | GLN | ASP | MET | THR | THR<br>165 | HIS | LEU | ILE |

-continued

```
            LEU ARG SER PHE LYS GLU PHE LEU GLN SER SER LEU ARG ALA
            170             175             180

LEU ARG GLN MET
            185
```

(2) INFORMATION FOR SEQ ID NO:3:

(i) SEQUENCE CHARACTERISTICS:
        (A) LENGTH: 187
        (B) TYPE: Amino acid
        (C) STRANDEDNESS:
        (D) TOPOLOGY: Linear     (xi) SEQUENCE DESCRIPTION: SEQ. ID. NO::3:

```
            MET LYS ALA PRO VAL PRO PRO GLY GLU ASP SER LYS ASP VAL
            -2  -1  1           5                   10

ALA ALA PRO HIS ARG GLN PRO LEU THR SER SER GLU ARG ILE
            15              20              25

ASP LYS GLN ILE ARG TYR ILE LEU ASP GLY ILE SER ALA LEU
            30              35              40

ARG LYS GLU THR CYS ASN LYS SER ASN MET CYS GLU SER SER
            45              50

LYS GLU ALA LEU ALA GLU ASN ASN LEU ASN LEU PRO LYS MET
            55              60              65

ALA GLU LYS ASP GLY CYS PHE GLN SER GLY PHE ASN GLU GLU
            70              75              80

THR CYS LEU VAL LYS ILE ILE THR GLY LEU LEU GLU PHE GLU
            85              90              95

VAL TYR LEU GLU TYR LEU GLN ASN ARG PHE GLU SER SER GLU
            100             105             110

GLU GLN ALA ARG ALA VAL GLN MET SER THR LYS VAL LEU ILE
            115             120

GLN PHE LEU GLN LYS LYS ALA LYS ASN LEU ASP ALA ILE THR
            125             130             135

THR PRO ASP PRO THR THR ASN ALA SER LEU LEU THR LYS LEU
            140             145             150

GLN ALA GLN ASN GLN TRP LEU GLN ASP MET THR THR HIS LEU
            155             160             165

ILE LEU ARG SER PHE LYS GLU PHE LEU GLN SER SER LEU ARG
            170             175             180

ALA LEU ARG GLN MET
            185
```

What is claimed is:

1. PEG-IL-6 having platelet forming activity wherein the IL-6 portion of the molecule has its naturally occurring complement of lysine residues and PEG is attached via one or more amino groups of IL-6.

2. The PEG-IL-6 of claim 1 wherein said IL-6 is a member selected from the group consisting of glycosylated IL-6, unglycosylated IL-6, and biologically active fragments thereof resulting from deletion of up to about 27 amino terminal amino acids and/or up to about 50 carboxy terminal amino acids.

3. The PEG-IL-6 of claim 2 wherein said IL-6 comprises a sequence of amino acids selected from the group of amino acid sequences as defined in the Sequence Listing by SEQ ID NO:1, SEQ ID NO:2, and SEQ ID NO:3.

4. The PEG-IL-6 of claim 3 wherein said IL-6 is a member selected from the group consisting of naturally produced and synthetically produced IL-6.

5. The PEG-IL-6 of claim 4 wherein said naturally produced IL-6 is the expression product of a prokaryotic or eukaryotic host cell transformed or transfected with a DNA sequence encoding IL-6 or encoding a biologically active IL-6 fragment.

6. The PEG-IL-6 of claim 5 wherein said host cell is E. coli.

7. The PEG-IL-6 of claim 1 wherein said PEG is obtained from activated PEG.

8. The PEG-IL-6 of claim 7 wherein said activated PEG is a member selected from the group consisting of the succinimidyl succinate derivative of PEG and the bis-PEG derivative of cyanuric chloride.

9. The PEG-IL-6 of claim 7 wherein said activated PEG is a member selected from the group consisting of activated PEG1, PEG2, and PEG12M.

10. The PEG-IL-6 of claim 1 wherein at least one hydrogen atom of said amino group on said IL-6 is substituted with said PEG.

11. The PEG-IL-6 of claim 1 selected from the group consisting of PEG1-IL-6, PEG2-IL-6, PEG12M-IL-6.

12. The PEG1-IL-6 of claim 11 that is PEG(4500)IL-6.

13. The PEG(4500)IL-6 according to claim 12 selected from the group consisting of Fr45-0, Fr45-1, Fr45-2, Fr45-3, Fr45-4, and Fr45-5.

14. The PEG2-IL-6 of claim 11 that is PEG(10000)IL-6.

15. The PEG(10000)IL-6 according to claim 14 selected from the group consisting of Fr100-0, Fr100-1, Fr100-2, Fr100-3, Fr100-4, and Fr100-5.

16. The PEG12M-IL-6 of claim 11 that is PEG(12000)IL-6.

17. The PEG(12000)IL-6 according to claim 16 selected from the group consisting of Fr120-1, Fr120-2, Fr120-3, Fr120-4, and Fr120-5.

18. The PEG12-IL-6 of claim 11 that is PEG(12000)IL-6'.

19. The PEG(12000)IL-6' according to claim 18 selected from the group consisting of Fr120'-1, Fr120'-2, Fr120'-3, Fr120'-4, and Fr120'-5.

20. A pharmaceutical composition for use in treatment of thrombocytopenia in an organism, said composition comprising a pharmaceutically acceptable solvent, diluent, adjuvant, or carrier and, as the active ingredient, from about 0.0001 mg to about 10 mg per kg of body weight of said organism of PEG-IL-6 according to claim 1.

* * * * *

UNITED STATES PATENT AND TRADEMARK OFFICE
CERTIFICATE OF CORRECTION

PATENT NO. : 5,264,209
DATED : November 23, 1993
INVENTOR(S) : Mikayama, Toshihumi et al.

It is certified that error appears in the above-identified patent and that said Letters Patent is hereby corrected as shown below:

At column 6, line 51, delete "$R^1$ and $R^2$" and substitute therefor --$R_1$ and $R_2$--;

At column 7, line 50, after "formula" insert --6--;

At column 7, line 51, after "formula" delete "6" and substitute therefor --7--;

At column 18, line 50, after "old" delete "(" and substitute therefor --,--;

At column 16, line 21, delete "IL-6" and substitute therefor --hIL-6--; and,

At column 16, line 62, delete "along" and substitute therefor --alone--.

Signed and Sealed this

Twentieth Day of September, 1994

Attest:

BRUCE LEHMAN

*Attesting Officer*      *Commissioner of Patents and Trademarks*